US006316664B1

(12) United States Patent
Kratz et al.

(10) Patent No.: US 6,316,664 B1
(45) Date of Patent: *Nov. 13, 2001

(54) PROCESS FOR PREPARING HYDROXY-CONTAINING COMPOUNDS FROM FORMIC ACID ESTERS

(75) Inventors: Detlef Kratz, Heidelberg; Christoph Sigwart, Schriesheim, both of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,338
(22) PCT Filed: Nov. 11, 1996
(86) PCT No.: PCT/EP96/04923
§ 371 Date: May 8, 1998
§ 102(e) Date: May 8, 1998
(87) PCT Pub. No.: WO97/17319
PCT Pub. Date: May 15, 1997

(30) Foreign Application Priority Data

Nov. 10, 1995 (DE) .............................. 195 42 035

(51) Int. Cl.$^7$ .......................... C07C 67/02; C07C 67/03; C07C 69/02; C07C 67/00
(52) U.S. Cl. .................. 560/217; 560/231; 560/234; 560/239
(58) Field of Search .................... 560/231, 239, 560/217, 234

(56) References Cited

U.S. PATENT DOCUMENTS

| 4,283,565 | * | 8/1981 | Bernhardt et al. | 568/648 |
| 4,448,946 | * | 5/1984 | Stutz et al. | 528/67 |
| 4,904,717 | * | 2/1990 | Ho et al. | 524/392 |
| 5,149,861 | * | 9/1992 | Merger et al. | 560/234 |

FOREIGN PATENT DOCUMENTS

| 24 60 039 | 12/1973 | (DE) . |
| 42 36 971 | 5/1994 | (DE) . |
| 0 168 167 | 6/1985 | (EP) . |
| 0 289 921 | 11/1988 | (EP) . |
| 0 503 386 | 2/1992 | (EP) . |

OTHER PUBLICATIONS

The Prins Reaction David R. Adams, Surendra P.Bhatnagar, pp. 661–672, Synthesis (1977).
J. S. Bajorel, R. Battaglia, G. Pratt, J. K. Sutherland, J. Chem. Soc. Perkin I pp. 1243–1245 (1974).
The Chemistry of Carboxylic acids and esters, Ed. S. Patai, 1969, p. 103 et seq.
Methoden der organischen Chemie (Houben–Weyl), vol E5, Georg–Thieme Verlag, Stuttgart 1985, p. 702 et seq.).

* cited by examiner

Primary Examiner—Gary Geist
Assistant Examiner—Everett White
(74) Attorney, Agent, or Firm—Oblon, Spivak, McClelland, Maier & Neustadt, P.C.

(57) ABSTRACT

Formic ester is transesterified with a hydroxyl-containing compound in the presence of a tertiary amine as transesterification catalyst to form a formic ester which differs from the formic ester used as reactant, and of a hydroxyl-containing compound which is different from the hydroxyl-containing compound used as reactant.

27 Claims, No Drawings

PROCESS FOR PREPARING HYDROXY-CONTAINING COMPOUNDS FROM FORMIC ACID ESTERS

The invention relates to a process for preparing hydroxyl-containing compounds (1), in particular alcohols, and formic esters of a hydroxyl containing compound (2) by transesterification of a formic ester (also "formate" hereinafter) of a hydroxyl containing compound (1) with a hydroxyl-containing compound (2), in particular alcohol, in the presence of a tertiary amine.

It is known to prepare esters $R^1COOR^3$ and/or hydroxyl-containing compound, in particular alcohol $R^2OH$, by transesterification of esters $R^1COOR^2$ with hydroxyl-containing compound, in particular alcohol $R^3OH$, according to the following scheme:

$$R^1COOR^2 + R^3OH \leftrightarrows R^1COOR^3 + R^2OH \quad \text{(Equation 1).}$$

Transesterification reactions of this type are described, for example, in The Chemistry of Carboxylic Acids and Esters, Ed. S. Patai, 1969, page 103 et seq.; Methoden der organischen Chemie (Houben-Weyl), Volume E5, Georg-Thieme Verlag, Stuttgart 1985, page 702 et seq. In the case where $R^1$ is H, the esters are of formic acid.

$$HCOOR^2 + R^3OH \leftrightarrows HCOOR^3 + R^2OH \quad \text{(Equation 2).}$$

Some selected reactions in which formic esters are produced or result in industrial processes and are subsequently transesterified in accordance with Equation 2 are listed below.

1. Formic esters are employed as protective group for alcohols in synthetic chemistry. To obtain the unprotected alcohol it is subsequently necessary to remove the protective group quantitatively.

2. Formic esters occur in industrial processes in which formic acid is used as acidic catalyst, and in which alcohols are produced or are present. Particularly in the case of high-boiling compounds or polymers, these esters are often difficult to remove from the required alcohols by a physical purification process such as recrystallization, extraction or distillation, because their physical properties are very similar to those of the free alcohols. This is why the chemical method of transesterification is used, for example, for purification. The transesterification must take place quantitatively, and catalyst residues must not remain in the product.

a) For example, polyoxybutylene glycol formate (polyTHF formate) is formed in the cationic polymerization of tetrahydrofuran (THF) in the presence of formic acid (EP-A-503 386). In order to obtain pure polyoxybutylene glycol (polyTHF), the formate group must be removed quantitatively.

b) Another use in polymer chemistry is the polymerization of vinyl formate to poly(vinyl formate). In order to obtain the industrial product poly(vinyl alcohol), the formate groups, which are present in equimolar amounts, must be removed quantitatively.

c) In the Prins reaction of olefins with formaldehyde, which is catalyzed by formic acid, large amounts of the formates of the alcohols which are formed are produced (D.R. Adams, S. P. Bhatnagar, Synthesis (1977) 661–672; J. S. Bajorek, R. Battaglia, G. Pratt, J. K. Sutherland, J. Chem. Soc. Perkin I (1974) 1243–1245). In order to obtain the alcohols, the ester must be cleaved during the workup.

3. In reactions which are carried out in the presence of formaldehyde there is frequently formation, by Cannizzaro reaction of two equivalents of formaldehyde, of one equivalent of methanol and one equivalent of formic acid. Formic acid is also produced by crossed Cannizzaro reaction of aldehydes with formaldehyde. Formic acid produced in this way readily forms, under the reaction conditions, unwanted formic esters as byproduct. In this case too it is necessary to remove the formates either by physical separation methods or by chemical reaction.

The reactions according to Equation 1 and Equation 2 are equilibrium reactions. Starting from the ester $R^1COOR^2$, the equilibrium can be shifted in favor of the required product, the ester $R^1COOR^3$ or the alcohol $R^2OH$, by either using one initial component in excess or, more preferably, removing one reaction component, the alcohol $R^2OH$ or ester $R^1COOR^3$ produced, for example by distillation or by crystallization, from the equilibrium.

It is known that addition of a catalyst is necessary to carry out the transesterification according to Equation 1 or Equation 2. Typical transesterification catalysts used in industry include sulfuric acid, p-toluenesulfonic acid, sodium hydroxide solution, sodium alcoholates, aluminum alcoholates, potassium cyanide as well as acidic or basic ion exchangers. However, these catalysts have a number of disadvantages (see: The Chemistry of Carboxylic Acids and Esters, Ed. S. Patai, 1969, page 103 et seq.; Methoden der organischen Chemie (Houben-Weyl), Volume E5, Georg-Thieme Verlag, Stuttgart 1985, page 702 et seq.).

1. The strong bases and acids used as catalyst may lead to numerous unwanted side reactions such as elimination, C-alkylation or polymerization.

2. If the required product is the alcohol $R^2OH$, when strongly basic inorganic compounds like sodium methanolate are used as catalyst there are losses of yield, since part of the alcohol remains bound as alcoholate.

3. Neutralization is necessary for removal of the catalyst and liberation of alcohols from their alcoholates. This produces inorganic salts which have to be removed from the required product. This leads to decomposition of the catalyst. The inorganic salt must be disposed of.

4. Isolation of the required product is particularly difficult when the required alcohol or ester is high-boiling, crystalline or a polymer. The resulting inorganic salt cannot always be removed without difficulty in this case. Distillation in the presence of an inorganic salt results in decomposition of the required alcohol or ester.

5. If acidic or basic ion exchangers are employed as catalyst, the reaction cannot be carried out at elevated temperatures because ion exchangers are, as a rule, decomposed at temperatures above 60–100° C. On the other hand, in this case too, one reaction component, eg. the alcohol $R^2OH$, may remain bound to the solid support, resulting in losses of yield. The useful life of ion exchangers is limited. Another disadvantage of heterogeneous catalysts is that they are unsuitable for reaction with compounds of low solubility, especially polymers.

6. If the transesterification is carried out in the presence of water, a competing reaction is observed in the form of hydrolysis of the ester to form alcohol and inorganic salt of the acid, eg. sodium formate in the case of formic acid. Removal of alcohols by distillation in the presence of formic esters is known to lead to losses of yield due to decomposition. In addition, when inorganic alcoholates are used as catalyst, water leads to formation of the free base and thus inactivation of the actual catalyst. For example, sodium hydroxide solution is formed from sodium alcoholate and water and is a far less effective catalyst.

EP-A-0 289 921 describes for example the transesterification of trimethylolalkane formate with methanol. It is possible to use as catalysts alkali metal or alkaline earth metal alcoholates. To obtain the required alcohol TMP it is necessary to remove the catalyst before further workup, either by ion exchanger or by neutralization with an acid. This results in decomposition of the catalyst, and the workup process becomes more costly. An inorganic salt, eg. sodium acetate or chloride, results as byproduct and must be disposed of.

The use of tertiary amines as transesterification catalysts is known for specific reactions.

DE-A 24 60 039 describes the transesterification of acetoxymethylpyridines with methanol to hydroxymethylpyridines and methyl acetate in the presence of the tertiary amine triethylamine. The alcohol which is formed, hydroxymethylpyridine, is stabilized by electron-attracting groups. The transesterification disclosed in DE-A 24 60 039 is restricted by the fact that only a selected acfivated acetic ester with primary alcohol functionality and pyridine substituents can be reacted with methanol.

The low reactivity of non-activated acetates on transesterification with methanol using tertiary amine bases as catalyst has been confirmed experimentally. In the attempt to transesterify a mixture of the mono-, di-and triacetates of 1,1,1-trimethylolpropane (TMP) to TMP and methyl acetate under the conditions described in DE-A 24 60 039 there was no detectable conversion to methyl acetate. The reaction likewise does not succeed on addition of a stronger base with an amidine structure such as 1,8-diazabicyclo[5.4.0]undec-7-ene (DBU). Only after addition of methanolic tetramethylammonium hydroxide, ie. of OH⁻ ions, is formation of methyl acetate observed, although with a very unsatisfactory conversion.

Another disadvantage of the process described in DE-A 24 60 039 is that the transesterification provides virtually no reaction with ethanol and completely fails with isopropanol.

EP-A-0 168 167 discloses the transesterification of ethyl acetate and porpylene carbonate with methanol using a heterogeneous amine-containing catalyst. The catalyst system consists of an organic compound which contains a VA group element, and of an insoluble solid as support. The organic compound containing the VA group element can be an amine or phosphine. The organic compound is, for example, an amidine, guanidine, mono-, di- or trialkylamine.

The yield of methyl acetate from the transesterification of ethyl acetate with methanol after a reaction time of 24 hours is only 27%. No statements are made about the useful life of the heterogeneous support.

Further disadvantages of the process disclosed in EP-A-0 168 167 are the complicated preparation of the catalyst and the restriction of application, because the reaction is carried out heterogeneously, to specific substrates which are soluble in the reaction medium.

It is an object of the present invention to provide a process for preparing a hydroxyl-containing compounds, in particular alcohols, and formic esters by transesterification of formic esters without the disadvantages and restrictions described above.

We have found that this object is achieved by a process for preparing hydroxyl-containing compounds and formic esters by transesterification, wherein formic esters of an organic hydroxyl-containing compound (1) and an organic hydroxyl-containing compound (2) are transesterified in the presence of a tertiary amine as transesterification catalysts to form the organic hydroxyl-containing compound (1) and formic esters of the hydroxyl-containing compound (2), where compounds (1) and (2) differ from one another. For example hydroxyl-containing compounds $R^2OH$ and formic esters $HCOOR^3$ are prepared by transesterifying formic esters of the formula $HCOOR^2$ and a compound of the formula $R^3OH$ in the presence of a tertiary amine as transesterification catalyst to form formic ester of the formula $HCOOR^3$ and a compound of the formula $R^2OH$, where $R^2$ and $R^3$ are organic radicals which differ from one another. The radicals $R^2$ and $R^3$ are organic substituents which are inert under the reaction conditions; they are not critical for the ability of the process to be carried out.

Preferred embodiments are described below.

The advantages of the process according to the invention are many.

1. The reaction takes place with high selectivity and high yield in respect of formic esters.

2. The reaction conditions and temperatures are mild. Very mild bases are used, and thus side reactions are avoided.

3. There is no loss of catalyst, in contrast to the inorganic and heterogeneous catalysts described above from the prior art. Recovery and recirculation are straightforward.

4. The reaction mixtures are worked up in a straightforward manner by distillation or crystallization. No neutralization step is necessary.

5. The reaction takes place quantitatively, even in the presence of water.

The hydroxyl-containing compound (2) used for the transesterification is preferably added relative to the hydroxyl groups in an amount which is at least stoichiometric relative to the formic ester groups to the formic ester of the hydroxyl-containing compound (1).

Transesterification of the formic ester from an organic hydroxyl-containing compound (1), e.g. $R^2OH$, in particular alcohol, and formic acid relative to the hydroxylgroups with at least equimolar amounts of another organic hydroxyl-containing compound (2) (with respect to the ester group), in particular alcohol $R^3OH$, preferably in a molar ratio of hydroxyl group to ester group of 1:10, in particular 1:5, in the presence of a tertiary amine takes place rapidly and with quantitative yield and is not restricted to particular formic esters like the reaction known from EP-A-0 289 921. It is possible, for example, according to one embodiment of the invention to convert the formates of trimethylolpropane with methanol in the presence of triethylamine quantitatively into TMP and methyl formate. Formic esters of secondary, tertiary and aromatic alcohols, such as cyclohexyl formate, tert-butyl formate, phenyl formate, likewise react after addition of methanol and tertiary amine base to give the alcohol and methyl formate.

The organic hydroxyl-containing compound (1) can have one or more hydroxyl groups, preferably 1 to 6, especially 1 to 3 hydroxyl groups. It can be a hydroxyl-containing polymer as well, e.g. a polyvinyl alcohol. It can have the formula $R^2OH$.

The $R^2$ radical in the formic ester of the formula $HCOOR^2$ to be transesterified is generally a saturated or unsaturated, branched or unbranched, linear, unsubstituted or substituted hydrocarbon radical which has preferably 1 to 30 carbon atoms, in particular 2 to 20 carbon atoms, particularly preferably 3 to 18 carbon atoms, and which contains, if required, ether group(s), ester group(s), hydroxyl group(s) or ketone group(s), or an aromatic hydrocarbon radical which has preferably 6 to 12 carbon atoms and which is substituted if required, or a cycloalkyl radical which has preferably 3 to 12, in particular 6 to 12, carbon atoms and which is substituted if required, or a heterocyclic radical which has preferably 3 to 12 carbon atoms and 1 to 3 nitrogen atoms and which is substituted if required, where the substituents are selected from benzyl, phenyl, cyclohexyl, pyridyl, methylpyridyl, hydroxyl, carboxyl, alkyl, the latter with preferably 1 to 12 carbon atoms.

$R^2$ is particularly preferably propyl, tert-butyl, a trimethylolpropane residue, cyclohexyl, phenyl, a neopentyl glycol hydroxypivalate residue, a polyoxybutylene residue, a ditrimethylolpropane residue or methylpyridyl.

The radical $R^2$ of the formic ester of the formula $HCOOR^2$ to be transesterified can also be functionalized by other radicals.

The tertiary amines used as transesterification catalysts can be compounds of the general structural formula $R^aR^bR^cN$. The radicals $R^a$, $R^b$, $R^c$ are identical or different. They are preferably, each independently of the others, a branched or unbranched alkyl radical preferably with 1 to 12, preferably 1 to 6, most preferably 1 to 3, carbon atoms, cycloalkyl radical preferably with 3 to 12, in particular 6 to 12, carbon atoms or aromatic hydrocarbon radical preferably with 6 to 12 carbon atoms, each of which can be substituted if required.

The tertiary amine can also be a heterocyclic tertiary nitrogen compound selected from heterocycloalkane, heterocycloalkene or heteroaromatic compound preferably with 3 to 12 carbon atoms and 1 to 3 nitrogen atoms.

The heterocyclic nitrogen compound preferably used is 1,4-diazabicyclooctane, N,N'-dialkylpiperazine, N-alkylpiperidine, N-alkylaziridine, N-alkylpyrrole, N-methylimidazole or 1,8-diazabicyclo[5.4.0]undec-7-ene.

The alkyl radical in the abovementioned compounds is preferably a branched or unbranched, linear alkyl radical preferably with 1 to 6, most preferably 1 to 4, carbon atoms.

The $pK_a$ of the tertiary amine should be greater than 5, preferably from 7 to 12. The choice of the amine can be adapted to suit the other reaction components without difficulty. The amines which are preferably used are those having a boiling point above the boiling point of the formic ester which is formed and the boiling point of the hydroxyl-containing compound (2) employed, in particular alcohol. If methanol is used for the transesterification, suitable amines have a boiling point above that of methyl formate and that of methanol, in particular trialkylamines such as triethylamine and tributylamine.

The transesterification catalyst is preferably unsupported or homogeneous. The transesterification catalyst is preferably added in liquid form.

The tertiary amine can be added in catalytic amounts of from 0.01 to 10 mol %, preferably from 0.1 to 5 mol %, based on formate group as 100 mol %.

An excess of tertiary amine going beyond the amount of formic acid equivalents present has no disadvantages because all the reaction components are recovered after the transesterification is complete. For example, volatile amines such as trimethylamine or triethylamine can easily be removed by distillation from the high-boiling alcohol and be reused. In the event that the amine used is higher-boiling than the alcohol (1) or $R^2OH$, the procedure can be reversed. The required alcohol (1) or $R^2OH$ is first removed from the tertiary amine by distillation. The remaining tertiary amine need not be worked up because the amine-containing residue can be employed again directly for the reaction. In certain cases, an excess of amine component is advantageous, especially when the amine is suitable as solvent for the reaction.

Examples of organic hydroxyl-containing compounds (2) used in the transesterification are alcohols having up to 6 hydroxyl groups, e.g. of the formula $R^3OH$.

In a preferred embodiment, the radical $R^3$ in the alcohol $R^3OH$ used for the transesterification is a saturated or unsaturated, branched or unbranched linear hydrocarbon radical which has preferably 1 to 20 carbon atoms, in particular 1 to 8 carbon atoms, particularly preferably 1 to 3 carbon atoms, an aromatic hydrocarbon radical which has preferably 6 to 12 carbon atoms or a cycloalkyl radical which has preferably 3 to 12, in particular 6 to 12, carbon atoms.

Examples of the alcohol $R^3OH$ used for the transesterification are cyclohexanol, methanol, ethanol, propanol, butanol, isopropanol, isobutanol, tert-butanol and benzyl alcohol.

The alcohols $R^2OH$ and $R^3OH$ can be primary, secondary or tertiary. The radicals $R^2$ and $R^3$ may carry further OH groups and thus the ester $HCOOR^2$ or $HCOOR^3$ may also have more than one formic ester group.

In the following the compound (1) is illustrated by $R^2OH$ and the compound (2) is illustrated by $R^1OH$. The illustration is valid as well for (1) and (2).

The range of application of the transesterification depends on the physical properties of the reaction components. It may be advantageous for the alcohol $R^2OH$ and the ester $HCOOR^2$ to be higher-boiling than the alcohol $R^3OH$ used for the transesterification and the ester $HCOOR^3$ produced therefrom, that is to say the boiling points are in the sequence $HCOOR^2 \approx R^2OH > R^3OH \geq HCOOR^3$.

Alcohols $R^3OH$ suitable to be employed in the transesterification to prepare purer products are those which are more volatile than the hydroxyl-containing compound formed, for example the alcohol $R^2OH$. $R^3$ can be a primary, secondary or tertiary functionality. If $R^3OH$ is less volatile than $R^2OH$, mixtures of products result.

Particularly suitable alcohols are those whose boiling point is higher than that of the corresponding formic ester $HCOOR^3$ which is formed, so that the formic ester formed during the transesterification can be removed from the equilibrium by distillation. It is possible in this way to avoid a large excess of alcohol. Likewise, the alcohol $R^3OH$ should, where possible, not form an azeotrope with the formic ester. However, even in a case of this type, the transesterification is possible by removing the low-boiling alcohol and formic esters together. Alcohols such as methanol, ethanol, propanol, butanol, isopropanol, isobutanol, tert-butanol are particularly suitable. Methanol is preferably employed because in this case there is a large difference in boiling point between alcohol and formic ester. To carry out the reaction quantitatively, $R^3OH$ is employed in amounts which are at least stoichiometric relative to the equivalents of formic acid. It is advantageous in certain cases to increase the amount of the alcohol $R^3OH$ because this then also acts as solvent for the ester $HCOOR^2$ to be transesterified or the alcohol $R^2OH$ which is formed. If the transesterification results in an alcohol $R^2OH$ which is crystalline and of low solubility in the reaction medium, the latter can be isolated after the reaction directly by crystallization from $R^3OH$ or the amine. In the case of a polymeric alcohol, this can be precipitated, for example from $R^3OH$.

In a preferred embodiment of the invention, a process for preparing alcohols by transesterification of a formic ester in accordance with Equation 2, where the alcohol $R^2OH$ and the ester $HCOOR^2$ are higher-boiling than the alcohol $R^3OH$ used for the transesterification and the ester $HCOOR^3$ produced therefrom, is made available.

The transesterification can be carried out either continuously or batchwise. The temperature used for the reaction depends on the boiling points of the reaction components.

The transesterification can be carried out under reduced pressure, under atmospheric pressure or under elevated pressure. In a preferred embodiment with methanol as transesterification reagent and triethylamine as catalyst, the formic ester $HCOOR^2$ is reacted under atmospheric pressure at from 35 to 65° C. In this case, the $HCOOR^2$/methanol/triethylamine molar ratio for the reaction components employed is 1/1–10/0.0005–0.1, in particular about 1/5/0.05. The amount of methanol can, however, be reduced to the amount corresponding to that of the formate. The methyl formate which is formed is removed continuously in a conventional distillation apparatus. A countercurrent column is suitable for the continuous procedure.

The transesterification can also be carried out in the presence of other inert solvents added to homogenize the reaction components. It is possible to employ, for example, acyclic and cyclic ethers such as tetrahydrofuran, dioxane and diethyl ether or aromatic compounds such as toluene, and esters which are stable to the reaction medium, such as ethyl acetate.

Another advantage of the process according to the invention is that the transesterification of formic esters $HCOOR^2$ can also be carried out completely in the presence of water.

In contrast to this, transesterification of formic esters of trimethylolpropane (TMP) with a 1:1 mixture of methanol and water based on volume with 10 mol % sodium hydroxide solution as catalyst does not take place quantitatively. Sodium formate is formed by hydrolysis, and the maximum conversion observed even on prolonged treatment with methanol is only 75% based on TMP formates. In addition, the sodium formate which is formed interferes with the isolation of TMP by distillation.

The range of applications of the transesterification which has been found is to be illustrated by examples.

The transesterification, according to the invention, of the formic esters takes place selectively in respect of the formate functionality in the presence of other ester functionalities. Mono- and diformic esters of neopentyl glycol hydroxypivalate (NHP), which are byproducts of the industrial production of NHP as described in, for example, DE 19 58 463 or DE 22 33 357, can be reacted selectively. Selective transesterification of these mono- and diformic esters of NHP is carried out according to the invention with a mixture of methanol and triethylamine to give NHP and methyl formate without cleavage of the central ester group of the NHP. NHP is obtained without losses after removal of excess methanol/triethylamine. By contrast, when typical "inorganic" transesterification catalysts such as sodium methanolate are used there is found to be formation of methyl hydroxypivalate and neopentyl glycol.

Formic esters of polymeric compounds can also be transesterified very well. For example, polytetrahydrofuran (polyTHF) which is esterified by formic acid on the alcoholic end groups (a product of the polymerization of THF with W catalysts and formic acid (EP-A-0 503 394)) can be converted with methanol and triethylamine as catalyst quantitatively into polyTHF by one embodiment. The purified polyTHF is isolated in a straightforward manner by removing methanol and triethylamine by distillation.

Surprisingly, when the inorganic base sodium hydroxide solution is replaced by a tertiary amine such as triethylamine the formates of TMP are converted almost quantitatively into TMP. Once again partial hydrolysis to formic acid, which is present in solution as triethylammonium formate, is observed. However, the reaction also takes place quantitatively at a pH <7. This means that catalysis by a tertiary amine such as triethylamine is superior to catalysis by sodium hydroxide solution. In addition, the reaction catalyzed by a tertiary amine has advantages owing to simplified workup because alcohols can be distilled undecomposed even in the presence of organic formic acid salts.

The invention is explained in detail by means of the following examples.

Comparative Example 1

This comparative example shows the low reactivity of unactivated acetates on transesterification with methanol.

132 g (0.75 mol) of a mixture of trimethylolpropane (TMP), TMP monoacetate, TMP diacetate and TMP triacetate (GC % areas=32/50.5/16/1.5) are dissolved in 240 g of methanol (7.5 mol). 38.5 g (0.38 mol) of triethylamine are added and the mixture is heated to reflux. A temperature of 65° C. is observed at the top of the column, and methyl acetate is undetectable. The percentage ratio of acetates in the bottom remains unchanged.

All the methanol and triethylamine are distilled out, and 200 ml of methanol and 22 g of 1,8-diazabicyclo[5.4.0]undec-7-ene (DBU) are added to the reaction mixture. No conversion of the acetates is observed after heating to reflux. The temperature at the top of the column is 65° C.

Finally, 20 g of a 25% strength aqueous tetramethylammonium hydroxide solution are added to the reaction mixture. The boiling point at the top of the column falls, and a mixture of methanol and methyl acetate can be distilled out. The conversion of the TMP acetates emerges from the analysis by gas chromatography: TMP 43%, TMP monoacetate 51%, TMP diacetate 6%, TMP triacetate 1%.

EXAMPLE 1a

Preparation of a mixture of the formic esters of 1,1,1-trimethylolpropane (TMP).

134 g of TMP are refluxed with 46 g of formic acid for 5 hours. The water which has formed is then distilled out. Finally, a mixture of TMP and the mono-, di- and triformates of TMP is distilled out. GC analysis reveals a ratio of 49/40/10/1.

EXAMPLE 1b 81 g (0.5 mol) of the mixture obtained from a) are dissolved in 64 g of methanol. 4 g of triethylamine are added and the mixture is stirred at an internal temperature of 40° C. GC analysis of the reaction mixture after 15 minutes reveals a composition of 80/18/2/-. The mixture is then heated, and methyl formate is distilled out until conversion is quantitative after one hour.

EXAMPLE 2

The procedure is as in Example 1b). In place of triethylamine, 4 g of 1,8-diazabicyclo[5.4.0]undec-7-ene (DBU) are used as catalyst. After 5 minutes, 95% TMP and 5% TMP monoformate are present. Quantitative conversion is achieved by distilling out methyl formate.

EXAMPLE 3

The procedure is as in Example 1b). The starting materials for the transesterification are 81 g of TMP formate mixture (Example 1a)), 80 g of methanol and 28.5 g of N,N'-dimethylpiperazine. After 2 hours, TMP formates are no longer detectable in the reaction mixture.

EXAMPLE 4

The procedure is as in Example 1b). The starting materials are 81 g of TMP formate mixture (Example 1a)), 80 g of methanol and 28.5 g of N-ethylpiperidine. After 2 hours, TMP formates are no longer detectable in the reaction mixture.

EXAMPLE 5

The procedure is as in Example 1b). The starting materials are 246 g of TMP formate mixture (Example 1a)), 370 g of ethanol and 76 g of triethylamine. The temperature at the top of the column is 54–55° C. (boiling point of ethyl formate). Distillation is continuous and, after 1 hour, the temperature increases to 78° C. The distillate contains 88.7% ethyl formate, 10.2% ethanol and 1.1% triethylamine. The conversion of TMP formates is 100%.

EXAMPLE 6

The procedure is as in Example 5. The starting materials are 246 g of TMP formate mixture (Example 1a)), 480 g of isopropanol and 76 g of triethylamine. The temperature at the top of the column is initially 72° C. Distillation is continuous and the temperature rises to 82° C. within 4 hours. The distillate contains 40% isopropyl formate, 35% isopropanol and 25% triethylamine. The conversion of the TMP formates is 100%.

EXAMPLE 7

The procedure is as in Example 5. The starting materials are 66.5 g of TMP formate mixture (Example 1a)), 148 g of tert-butanol and 19 g of triethylamine. The temperature at the top of the column is initially 77° C. Distillation is continuous and the temperature rises to 82° C. within 1 hour. The distillate contains 15% tert-butyl formate, 70% tert-butanol and 15% triethylamine. The conversion of the TMP formates is 100%.

EXAMPLE 8

42 g of a mixture of cyclohexanol and cyclohexyl formate (65/35) are dissolved in 64 g of methanol. 20 g of triethylamine are added and the mixture is heated to boiling, and methyl formate is distilled out continuously through a column. The cyclohexanol to cyclohexyl formate ratio after 4 hours is 97.5/2.5.

EXAMPLE 9

The procedure is as in Example 8 but with the following starting materials: 15 g of a mixture of tert-butanol and tert-butyl formate (97.8/1.2), 32 g of methanol, 10 g of triethylamine. The ratio of tert-butanol to tert-butyl formate after 4 hours is 99.1/0.9.

EXAMPLE 10

The procedure is as in Example 8 but with the following starting materials: 82.4 g of a mixture of neopentyl glycol hydroxypivalate (NHP) and neopentyl glycol hydroxypivalate mono- and diformates (94.5/3.2/2.3), 65 g of methanol, 4 g of triethylamine. The mixture is stirred at 40° C. for 2 hours. The formation of methyl formate is established by gas chromatography. The NHP components are present in a ratio of 98.8/1.2/-. Complete conversion of the NHP formates is achieved by distilling out methyl formate and methanol. No other additional components can be detected.

Comparative Example 2

The procedure is as in Example 1b). The starting materials are 243 g of TMP formate mixture (Example 1a)), 240 g of methanol, 135 g of water and 6 g of NaOH. The pH of the solution decreases during the reaction from 9.8 to 5.3. At a bottom temperature of 65° C., methyl formate is distilled out at a temperature at the top of the column of 35° C. The temperature at the top increases to 65° C. after 1 hour. The composition of the reaction solution reveals a ratio of TMP and mono-, di- and triformates of 83/16/1/-.

EXAMPLE 11

The procedure is as in Comparative Example 2. The starting materials are 243 g of TMP formate mixture (Example 1a)), 240 g of methanol, 135 g of water and 15 g of triethylamine. The pH of the solution falls during the reaction (3 hours) from 10.2 to 5.3. At a bottom temperature of 65° C., methyl formate is distilled out at a temperature at the top of the column of 35° C. The temperature at the top increases to 65° C. after 3 hours. The composition of the reaction solution reveals a ratio of TMP and mono-, di- and triformates of 96.5 13.5/-/-.

EXAMPLE 12

PolyTHF monoformate (prepared by polymerization of THF catalyzed by $H_3PW_{12}O_{40}$ in the presence of formic acid as described in EP-A-503 394) employed as precursor had the following characteristics:

$M_n$=1030(from OH value and SV);

SV=55 mg KOH/g; OH value=54 mg KOH/g.

500 g of polyTHF monoformate 1030 (0.5 mol) were dissolved in 480 g of methanol (15 mol) in a distillation apparatus. 5 g of triethylamine (0.05 mol; previously distilled under argon) were added and the reaction mixture was then heated to 67° C. (bottom temperature). Methyl formate (boiling point 32° C.) which was formed was distilled out through a Vigreux column until the temperature at the top was 65° C. To remove excess methanol, catalyst and low molecular weight oligomers, the residue was concentrated at 40° C. under reduced pressure and then subjected to short-path distillation at 230° C./0.5 mbar.

The polyTHF remaining as distillation residue (440 g) had the following characteristics:

$M_n$=1170 (OH value);

OH value=96 mg KOH/g; SV=0.3 mg KOG/g; residual N content=5 ppm (determination method: chemical luminescence; detection limit about 1 ppm; ref.: "Quantitative Organische Elementaranalyse", Friedrich Ehrenberger, VCH Weinheim, 1991, page 382 et seq.; apparatus used: DN 1000 from Dohrmann) The conversion calculated from the SV is 99.5%; Abbreviations:

OH value=hydroxyl value; SV=saponification value;

$M_n$=number average molecular weight as enclosed to IPER.

We claim:

1. A process for preparing a hydroxyl-containing compound of the formula $R^2OH$ and a formic ester of a hydroxy-containing compound of the formula $R^3OOCH$, comprising transesterifying a formic ester of an organic hydroxyl-containing compound having the formula $R^2OOCH$ and an organic hydroxyl-containing compound of the formula $R^3OH$ in the presence of a transesterification catalyst according to the equation:

$$R^2OOCH+R^3OH \leftrightharpoons R^3OOCH+R^2OH$$

wherein the transesterification catalyst consists essentially of a tertiary amine catalyst selected from the group consisting of a tertiary amine having the formula $R^aR^bR^cN$, wherein $R^a, R^b$ and $R^c$ are each, independently, optionally substituted branched or unbranched alkyl, optionally substituted cycloalkyl or optionally substituted aromatic hydrocarbon; and wherein $R^2$ is an optionally substituted, branched or linear $C_1$–$C_{30}$ alkyl, $C_6$–$C_{12}$ aromatic hydrocarbon or $C_3$–$C_{12}$ cycloalkyl; and $R^3$ is an organic group.

2. The process of claim 1, wherein $R^3$ is a saturated or unsaturated, branched or unbranched $C_1$–$C_{20}$ alkyl, $C_6$–$C_{12}$ aromatic hydrocarbon or $C_3$–$C_{12}$ cycloalkyl.

3. The process of claim 2, wherein $R^3$ is selected from the group consisting of cyclohexyl, methyl, ethyl, propyl, butyl, isopropyl, isobutyl, tert-butyl and benzyl.

4. The process of claim 1, wherein $R^2$ is selected from the group consisting of propyl, tert-butyl, trimethylolpropyl, cyclohexyl, phenyl, neopentyl glycol hydroxypivalyl, polyoxybutylenyl, ditrimethylolpropyl and methylpyridyl.

5. The process of claim 1, wherein the radicals $R^a, R^b, R^c$ are each, independently, optionally substituted branched or unbranched alkyl having 1 to 12 carbon atoms, or optionally substituted cycloalkyl having 3 to 12 carbon atoms, or optionally substituted aromatic hydrocarbon having 6 to 12 carbon atoms.

6. The process of claim 5, wherein the optionally substituted branched or unbranched alkyl has 1 to 6 carbon atoms, and the optionally substituted cycloalkyl has 6 to 12 carbon atoms.

7. The process of claim 6, wherein the optionally substituted branched or unbranched alkyl has 1 to 3 carbon atoms.

8. The process of claim 1, wherein the hydroxyl-containing compound $R^3OH$ is used in at least a stoichiometric amount relative to the formic ester of the hydroxyl-containing compound $R^2OOCH$, based on the formic ester groups.

9. The process of claim 1, wherein the formic ester of an organic hydroxyl-containing compound $R^2OOCH$, is a formic ester of polytetrahydrofuran, a formic ester of trimethylolpropane, a formic ester of neopentyl glycol hydroxypivalate, or a formic ester of polyvinyl alcohol.

10. The process of claim 9, wherein the formic ester of polytetrahydrofuran is the terminal monoformic ester.

11. The process of claim 10, wherein the tertiary amine is used in an amount from 0.1 to 5 mol %, based on the formic ester groups as 100 mol %.

12. The process of claim 1, wherein the tertiary amine is used in an amount of 1 to 10 mol %, based on the formic ester groups as 100 mol %.

13. The process of claim 1, wherein $R^3$ is unsaturated, branched or unbranched, linear alkyl having 1 to 8 carbon atoms or cycloalkyl of 6 to 12 carbon atoms.

14. The process of claim 13, wherein $R^3$ is unsaturated, branched or unbranched, linear hydrocarbon having 1 to 3 carbon atoms.

15. The process of claim 1, wherein the hydroxyl-containing compound $R^2OH$, and the ester $HCOOR^2$ each have a higher boiling point than the hydroxyl-containing compound $R^3OH$ used for the transesterfication and the ester $HCOOR^3$ produced therefrom.

16. The process of claim 1, wherein said transesterification catalyst is unsupported or homogeneous.

17. The process of claim 16, wherein said transesterification catalyst is added in liquid form.

18. The process of claim 1, wherein said tertiary amine is trimethylamine, triethylamine or tributylamine.

19. The process of claim 18, wherein said tertiary amine is triethylamine.

20. The process of claim 1, which comprises reacting formic ester $R^2OOCH$ with methanol in the presence of triethylamine at atmospheric pressure at a temperature of from 35 to 65° C.

21. The process of claim 20, wherein said formic ester $R^2OOCH$/methanol/triethylamine are used in a ratio of 1/1–10/0.0005–0.1.

22. The process of claim 21, wherein said formic ester $R^2OOCH$/methanol/triethylamine are used in a ratio of 1/5/0.05.

23. The process of claim 1, which is conducted in the presence of water.

24. The process of claim 1, which is conducted in a solvent to homogenize reaction components.

25. The process of claim 24, wherein said solvent comprises dioxane, tetrahydrofuran, diethylether, toluene or ethyl acetate.

26. The process of claim 1, which is conducted by batch.

27. The process of claim 1, which is conducted continuously with a countercurrent column.

* * * * *